United States Patent
Nanmyo et al.

(10) Patent No.: US 8,304,580 B2
(45) Date of Patent: Nov. 6, 2012

(54) METHOD FOR PRODUCING TRIS(PER-FLUORO-ALKANESULFONYL)METHIDE ACID SALT

(75) Inventors: Tsutomu Nanmyo, Ube (JP); Shintaro Sasaki, Ube (JP); Takashi Kume, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 528 days.

(21) Appl. No.: 12/520,178

(22) PCT Filed: Dec. 18, 2007

(86) PCT No.: PCT/JP2007/074296
§ 371 (c)(1),
(2), (4) Date: Jun. 19, 2009

(87) PCT Pub. No.: WO2008/075672
PCT Pub. Date: Jun. 26, 2008

(65) Prior Publication Data
US 2010/0022803 A1    Jan. 28, 2010

(30) Foreign Application Priority Data

Dec. 20, 2006 (JP) ................................ 2006-342043
Dec. 7, 2007 (JP) ................................ 2007-317315
Dec. 17, 2007 (JP) ................................ 2007-324490

(51) Int. Cl.
*C07C 315/00* (2006.01)
(52) U.S. Cl. ........................................................ 568/35
(58) Field of Classification Search ............... 568/35
See application file for complete search history.

(56) References Cited

U.S. PATENT DOCUMENTS 5,273,840 A * 12/1993 Dominey ..................... 429/307
6,410,190 B1 * 6/2002 Ignatiev et al. ............... 429/347
6,664,380 B1   12/2003 Barrett et al.

FOREIGN PATENT DOCUMENTS

| EP | 0813521 B1 * | 9/2000 |
| JP | 2000-226392 A | 8/2000 |
| JP | 2000-256348 A | 9/2000 |
| JP | 2000-256348 A * | 9/2000 |

OTHER PUBLICATIONS

English translation of JP-2000-256348-A; "machine translation" from JPO link at: http://www4.ipdl.inpit.go.jp/Tokujitu/tjsogodbenk.ipdl accessed Oct. 25, 2011; relevant part of document.*
European Search Report dated Jun. 8, 2011 (four (4) pages).
Waller et al., "Tris (trifluoromethanesulfonyl) methide ("Triflide") Anion: Convenient Preparation, X-ray Crystal Structures, and Exceptional Catalytic Activity as a Counterion with Ytterbium (III) and Scandium (III)", Journal of Organic Chemistry, vol. 64, 1999, pp. 2910-2913, XP-002636992.
Turowsky et al., "Tris ((trifluoromethyl) sulfonyl) methane, HC(SO2CF3)3", Journal of Inorganic Chemistry, vol. 27, 1988, pp. 2135-2137, XP-002636993.
International Search Report and PCT/ISA/237 w/translation dated Feb. 12, 2008 (Seven (7) pages).
Lutz Turowsky et al., "Tris((trifluoromethyl)sulfonyl)methane, $HC(SO_2CF_3)_3$", American Chemical Society, 1988, Inorg. Chem., vol. 27, No. 12, pp. 2135-2137.
A. Y. Il'Chenko, Tetraheterosubstituted Methanes with a Carbon-Halogen Bond, Science of Synthesis, 2005, pp. 1135-1201.
Djamila Benrabah et al., "Comparative Electrochemical Study of New Poly(oxyethylene)-Li Salt Complexes", Journal of the Chemical Society, Faraday Transactions, 1993, vol. 89, No. 2, pp. 355-359.

* cited by examiner

*Primary Examiner* — Shailendra Kumar
(74) *Attorney, Agent, or Firm* — Crowell & Moring LLP

(57) ABSTRACT

There is provided a method for producing a tris(perfluoroalkanesulfonyl)methide acid salt represented by formula [1], including the steps of (a) reacting a methylmagnesium halide represented by formula [2] with a perfluoroalkanesulfonyl fluoride represented by formula [3], thereby obtaining a reaction mixture; and (b) directly reacting the obtained reaction mixture with at least one selected from the group consisting of alkali metal halides, quaternary ammonium salts, and quaternary phosphonium salts. By this method, it is possible to easily produce the target methide acid salt with high yield.

17 Claims, No Drawings

METHOD FOR PRODUCING TRIS(PERFLUOROALKANESULFONYL)METHIDE ACID SALT

This application is a 371 of PCT/JP2007/074296, filed Dec. 18, 2007.

TECHNICAL FIELD

The present invention relates to a method for producing a tris(perfluoroalkanesulfonyl)methide acid salt.

BACKGROUND OF THE INVENTION

Tris(perfluoroalkanesulfonyl)methide acid salt is a substance that is useful as a Lewis acid catalyst or ion conducting material in the fields of organic syntheses, cell electrolyte, etc. Hitherto, there have been known many of the method for producing a tris(perfluoroalkanesulfonyl)methide acid salt, which is the target of the present invention. For example, Non-patent Publication 1 discloses that a tris(perfluoroalkanesulfonyl)methide acid salt is obtained by reacting trifluoromethanesulfonyl fluoride with a methylmagnesium halide (Grignard reagent).

Furthermore, Patent Publication 1 discloses a method for obtaining a methide acid salt by conducting a reaction between a perfluoroalkanesulfonyl halide and an alkali metal methane in organic solvent.

Non-patent Publication 1: Inorg. Chem., Vol. 27, pages 2135-2137, 1988
Patent Publication 1: Japanese Patent Application Publication 2000-226392

SUMMARY OF THE INVENTION

In the method of Non-patent Publication 1, as shown in the following scheme, a methide acid magnesium bromide salt produced by a reaction between a Grignard reagent and trifluoromethanesulfonyl fluoride is once turned into a methide acid by sulfuric acid, and furthermore a metal carbonate (herein cesium carbonate) causes this to obtain a methide acid salt (Scheme 1).

[Chemical Formula 1]

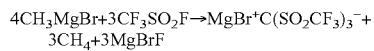

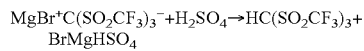

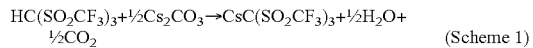

(Scheme 1)

This method, however, has had a burden on productivity and a difficulty somewhat industrially, since the reaction steps are long and since waste treatment takes time due to use of sulfuric acid.

On the other hand, in Patent Publication 1, it is a production method, in which a methide acid salt is obtained by one step, and therefore is a very useful method, in contrast with Non-patent Publication 1. This method, however, has had a difficulty in industrial production due to that the alkyl metal methane has a high price, that there is a problem of waste since it is treated with hydrochloric acid after the reaction, and that the reaction is conducted at around −55° C.

It is an object of the present invention to provide a method for producing a tris(perfluoroalkanesulfonyl)methide acid salt industrially more easily with a lower cost, as compared with conventional production methods.

According to the present invention, there is provided a method for producing a tris(perfluoroalkanesulfonyl)methide acid salt represented by formula [1]

[Chemical Formula 2]

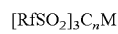  [1]

[In the formula, Rf represents a $C_{1-9}$ straight-chain or branched-chain perfluoroalkyl group, n represents an integer that is identical with valence of the corresponding cation, and M is a cation representing an alkali metal, quaternary ammonium represented by $(R^1)_4N$, or quaternary phosphonium represented by $(R^1)_4P$. Herein, $R^1$'s represent $C_{1-9}$, identical or different, straight-chain or branched-chain, saturated or unsaturated aliphatic hydrocarbon groups or aryl groups (herein, the hydrogen atoms may partially or entirely be replaced with halogen (fluorine, chlorine, bromine, or iodine), alkyl group, amino group, nitro group, acetyl group, cyano group or hydroxyl group)], comprising the steps of:

(a) reacting a methylmagnesium halide represented by formula [2]

[Chemical Formula 3]

$CH_3MgX$  [2]

[In the formula, X represents a chlorine, bromine or iodine.] with a perfluoroalkanesulfonyl fluoride represented by formula [3]

[Chemical Formula 4]

$RfSO_2F$  [3]

[In the formula, Rf represents a $C_{1-9}$ straight-chain or branched-chain perfluoroalkyl group.], thereby obtaining a reaction mixture; and (b) directly reacting the obtained reaction mixture with at least one selected from the group consisting of alkali metal halides, quaternary ammonium salts, and quaternary phosphonium salts.

We have found that a tris(perfluoroalkanesulfonyl)methide acid salt is obtained with short steps and with high purity and high yield, thereby completing the present invention.

According to the method described in Non-patent Publication 1, after a reaction between methylmagnesium halide and perfluoroalkanesulfonyl fluoride, a tris(perfluoroalkanesulfonyl)methide acid magnesium halide represented by formula [4]

[Chemical Formula 5]

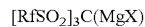  [4]

[In the formula, Rf is the same as above, and X represents a chlorine, bromine or iodine.]
of a methide acid magnesium bromide salt and the like, which is the obtained reaction mixture, is reacted with sulfuric acid, thereby producing a tris(perfluoroalkanesulfonyl)methide acid represented by formula [5]

[Chemical Formula 6]

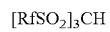  [5]

[In the formula, Rf is the same as above.]
and a metal carbonate (herein cesium carbonate) causes this to obtain a tris(perfluoroalkanesulfonyl)methide acid salt represented by formula [1]. In this method, however, a burden is placed on productivity, and furthermore purity and yield of the target product lower. Thus, there has been a difficulty even in industrial production.

The present inventors, however, have obtained surprising findings that the target product can be obtained by short steps, easily, and with high selectivity and high yield by directly reacting a tris(perfluoroalkanesulfonyl)methide acid magnesium halide with an alkali metal halide (cesium chloride, potassium chloride, or the like), a quaternary ammonium salt (tetramethylammonium bromide or the like), or a quaternary phosphonium salt (tetrabutylphosphonium bromide or the like), without going through a tris(perfluoroalkanesulfonyl)methide acid (Scheme 2).

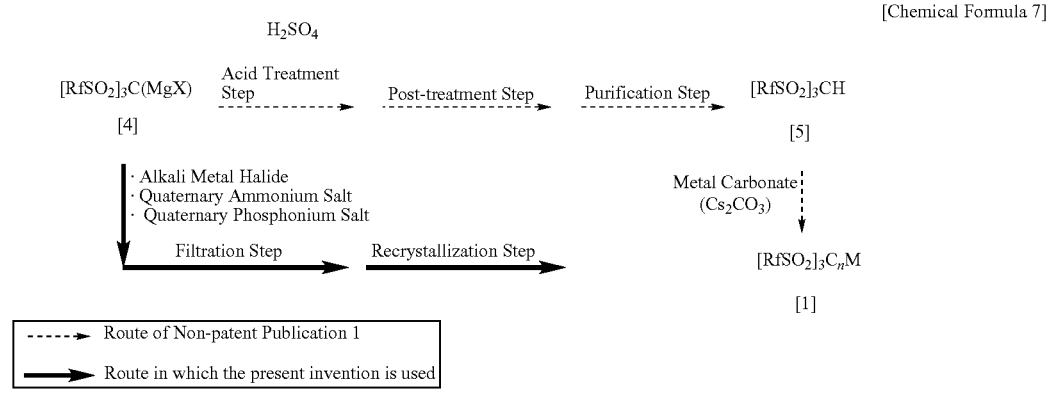

[Chemical Formula 7]

In the route in which the present invention is used, it is possible to greatly shorten the steps as compared with the past, and an acid such as sulfuric acid is not used. Therefore, it has become possible to greatly reduce a waste liquid, such as waste organic solvent and waste water, which is discharged in the post-treatment step. Furthermore, it has become possible to easily obtain the target product by methods that are even industrially easy, such as filtration and recrystallization.

Thus, it is possible to greatly simplify the steps and the production time. Therefore, it is also possible to easily supply the target product without taking much effort in operation, and it is a very excellent method in terms of production in industrial scale.

DETAILED DESCRIPTION

According to the present invention, it is possible to produce a tris(perfluoroalkanesulfonyl)methide acid salt, which is useful as organic synthesis and a cell electrolyte, more easily and with higher purity and higher yield as compared with the past. Furthermore, it achieves an effect that can greatly reduce waste liquid, such as waste organic solvent and waste water, which is discharged upon production.

In the following, the present invention is explained in more detail. As specific compounds of methylmagnesium halide represented by formula [2], it is possible to use methylmagnesium iodide, methylmagnesium bromide, and methylmagnesium chloride. Methylmagnesium chloride is preferable.

It is possible to produce methylmagnesium halide, which becomes the raw material, by a conventional publicly known method, but it is also possible to use one on the market as the product. A person skilled in the art can suitably select it.

As an organic solvent usable, an inert solvent is preferable that does not react with the raw materials and the product during the reaction step. It is possible to cite, for example, ethers such as diethyl ether, diisopropyl ether, t-butoxymethane, ethylene glycol dimethyl ether, tetrahydrofuran, and dioxane, and the like. The amount of the solvent used is suitably selected normally from the range of 0.5-10 times by volume, preferably from the range of 5-7 times by volume, methylmagnesium halide represented by formula [2].

For the perfluoroalkanesulfonyl fluoride represented by formula [3], a $C_{1-9}$ straight-chain or branched-chain perfluoroalkyl group is normally used, preferably $C_{1-6}$, particularly preferably $C_1$ (trifluoromethyl group). As specific compounds, it is possible to cite trifluoromethanesulfonyl fluoride, pentafluoroethanesulfonyl fluoride, heptafluoropropanesulfonyl fluoride, nonafluorobutanesulfonyl fluoride, undecafluoropentanesulfonyl fluoride, tridecafluorohexanesulfonyl fluoride, pentadecafluoroheptanesulfonyl fluoride, heptadecafluorooctanesulfonyl fluoride, nonadecafluorononanesulfonyl fluoride, and the like. Trifluoromethanesulfonyl fluoride, pentafluoroethanesulfonyl fluoride, heptafluoropropanesulfonyl fluoride, nonafluorobutanesulfonyl fluoride, undecafluoropentanesulfonyl fluoride, and tridecafluorohexanesulfonyl fluoride are preferable. Trifluoromethanesulfonyl fluoride is particularly preferable.

The amount of the perfluoroalkanesulfonyl fluoride is normally 0.75 to 2.0 moles, preferably 0.75 moles to 1.20 moles, particularly preferably 0.8 moles to 1.0 mole, relative to 1 mole of the methylmagnesium halide.

The present reaction is possible in a temperature range of $-78°$ C. to $100°$ C., preferably $-10°$ C. to $60°$ C. In the case of using a perfluoroalkanesulfonyl fluoride of low-boiling-point, it is preferable to conduct that under pressurization, to maintain the reactor at low temperature, or to conduct that by using a condenser of low-temperature.

In the case of conducting the reaction under pressurization, the reactor is charged with methylmagnesium halide represented by formula [2] and solvent, then the reactor is sealed, and perfluoroalkanesulfonyl fluoride is added. The addition is conducted, while suitably purging methane produced as a by-product, in order to control pressure.

The pressure is normally 0.1-10 MPa (absolute pressure, hereinafter the same), preferably 0.1-5 MPa, more preferably 0.1-2 MPa.

As to a reactor used upon conducting the reaction under pressurization, it is possible to conduct that by using a metal container such as stainless steel, Hastelloy, and Monel. In the case of conducting the reaction under ordinary pressure, a person skilled in the art can make a suitable selection regarding the reactor, too.

In the present invention, the obtained reaction mixture is reacted with at least one selected from the group consisting of alkali metal halides, quaternary ammonium salts, and quaternary phosphonium salts, thereby obtaining tris(perfluoroalkanesulfonyl)methide acid salt represented by formula [1].

As the alkali metal, it is possible to cite at least one selected from the group consisting of lithium (Li), sodium (Na), potassium (K), rubidium (Rb), and cesium (Cs).

As specific compounds of the alkali metal halide used in the present invention, it is possible to cite at least one selected from the group consisting of lithium fluoride, lithium chloride, lithium bromide, lithium iodide, sodium fluoride, sodium chloride, sodium bromide, sodium iodide, potassium fluoride, potassium chloride, potassium bromide, potassium iodide, rubidium fluoride, rubidium chloride, rubidium bromide, rubidium iodide, cesium fluoride, cesium chloride, cesium bromide, and cesium iodide. Sodium fluoride, sodium chloride, sodium bromide, sodium iodide, potassium fluoride, potassium chloride, potassium bromide, potassium iodide, rubidium fluoride, rubidium chloride, rubidium bromide, rubidium iodide, cesium fluoride, cesium chloride, cesium bromide, and cesium iodide are preferable. Potassium fluoride, potassium chloride, potassium bromide, potassium iodide, rubidium fluoride, rubidium chloride, rubidium bromide, rubidium iodide, cesium fluoride, cesium chloride, cesium bromide, and cesium iodide are particularly preferable.

As the quaternary ammonium salt used in the present invention, it is possible to cite $(R^1)_4N^+ \cdot X^-$ (in the formula, $R^1$'s represent $C_{1-9}$, identical or different, straight-chain or branched-chain, saturated or unsaturated aliphatic hydrocarbon groups or aryl groups (herein, the hydrogen atoms may partially or entirely be replaced with halogen (fluorine, chlorine, bromine, or iodine), alkyl group, amino group, nitro group, acetyl group, cyano group or hydroxyl group), X represents a halogen (fluorine, chlorine, bromine, or iodine), acetate, alkanesulfonate, or arylsulfonate (herein, the hydrogen atoms may partially or entirely be replaced with halogen (fluorine, chlorine, bromine, or iodine), alkyl group, amino group, nitro group, acetyl group, cyano group or hydroxyl group). Of these, $C_{1-7}$ is preferable, and $C_{1-4}$ is particularly preferable.

As the quaternary ammonium salt, it is possible to use those combined at random, which correspond to the above-mentioned formula. Of those, it is preferable to use tetramethylammonium fluoride, tetramethylammonium chloride, tetramethylammonium bromide, tetramethylammonium iodide, tetraethylammonium fluoride, tetraethylammonium chloride, tetraethylammonium bromide, tetraethylammonium iodide, tetrapropylammonium fluoride, tetrapropylammonium chloride, tetrapropylammonium bromide, tetrapropylammonium iodide, tetrabutylammonium fluoride, tetrabutylammonium chloride, tetrabutylammonium bromide, and tetrabutylammonium iodide.

As the quaternary phosphonium salt used in the present invention, it is possible to cite $(R^1)_4P^+ \cdot X^-$ (in the formula, $R^1$'s represent $C_{1-9}$, identical or different, straight-chain or branched-chain, saturated or unsaturated aliphatic hydrocarbon groups or aryl groups (herein, the hydrogen atoms may partially or entirely be replaced with halogen (fluorine, chlorine, bromine, or iodine), alkyl group, amino group, nitro group, acetyl group, cyano group or hydroxyl group), X represents a halogen (fluorine, chlorine, bromine, or iodine), acetate, alkanesulfonate, or arylsulfonate (herein, the hydrogen atoms may partially or entirely be replaced with halogen (fluorine, chlorine, bromine, or iodine), alkyl group, amino group, nitro group, acetyl group, cyano group or hydroxyl group). Of these, $C_{1-7}$ is preferable, and $C_{1-4}$ is particularly preferable.

As the quaternary phosphonium salt, it is possible to use those combined at random, which correspond to the above-mentioned formula. Of those, it is preferable to use tetraphenylphosphonium fluoride, tetraphenylphosphonium chloride, tetraphenylphosphonium bromide, tetraphenylphosphonium iodide, tetrabutylphosphonium fluoride, tetrabutylphosphonium chloride, tetrabutylphosphonium bromide, tetrabutylphosphonium iodide, butyltriphenylphosphonium fluoride, butyltriphenylphosphonium chloride, butyltriphenylphosphonium bromide, butyltriphenylphosphonium iodide, trioctylethylphosphonium fluoride, trioctylethylphosphonium chloride, trioctylethylphosphonium bromide, trioctylethylphosphonium iodide, benzyltriphenylphosphonium fluoride, benzyltriphenylphosphonium chloride, benzyltriphenylphosphonium bromide, benzyltriphenylphosphonium iodide, ethyltriphenylphosphonium fluoride, ethyltriphenylphosphonium chloride, ethyltriphenylphosphonium bromide, and ethyltriphenylphosphonium iodide.

In the present invention, methylmagnesium halide represented by formula [2] is reacted with perfluoroalkanesulfonyl fluoride represented by formula [3]. Then, the obtained reaction mixture is directly added to an aqueous solution dissolving at least one selected from the group consisting of alkali metal halides, quaternary ammonium salts, and quaternary phosphonium salts to conduct a reaction. After the reaction, the solvent used is distilled out. With this, the target tris(perfluoroalkanesulfonyl)methide acid salt is precipitated.

In the present invention, although details are described hereinafter in Examples, it is possible to easily obtain the methide acid salt with high purity by even industrially easy methods that are filtration and recrystallization.

Then, the filtration step is explained. The filtration step is not particularly limited. Upon this, in the case of a tris(perfluoroalkanesulfonyl)methide acid salt that has low solubility in water, the crystals are precipitated after distilling the solvent out. Therefore, it can be isolated by filtration.

On the other hand, in the case of a salt having high solubility, an extraction is conducted by using a solvent having high solubility to the tris(perfluoroalkanesulfonyl)methide acid salt, for example, an organic solvent such as ethyl acetate, isopropyl ether, or diethyl ether, and the solvent is distilled out. Then, the after-mentioned recrystallization operation is conducted. With this, it is possible to obtain a tris(perfluoroalkanesulfonyl)methide acid salt of high purity.

It is possible to easily remove inorganic salts, which are contained in the methide acid salt and are derived from methylmagnesium halide and alkali metal halide, by conducting the filtration step.

Next, the recrystallization step is explained. Regarding the recrystallization step too, there is no particular limitation. As the recrystallization solvent to be used, organic solvent or water can be cited. As the organic solvent, it can be exemplified by, for example, ethers such as diethyl ether, tetrahydrofuran, dioxane, butyl methyl ether, diisopropyl ether, and ethylene glycol dimethyl ether; alcohols such as methanol, ethanol, n-propyl alcohol, iso-propyl alcohol, n-butyl alcohol, iso-butyl alcohol, sec-butyl alcohol, and tert-butyl alcohol; alkanes such as n-pentane, n-hexane, n-heptane, and n-octane; alkyl ketones such as acetone, methyl ethyl ketone, and methyl isobutyl ketone; halogenated hydrocarbons such as dichloromethane and chloroform; and aromatics such as benzene, toluene, and xylene. Each of these organic solvents may be used alone, and a plurality of the organic solvents may be combined.

Of these, as shown in the after-mentioned Examples, even in the case of a recrystallization using water as solvent, it is possible to obtain a tris(perfluoroalkanesulfonyl)methide acid salt of a sufficiently high purity. Therefore, a recrystallization using water is one of particularly preferable embodiments in the industrial production method of the present invention.

By recrystallization, tris(perfluoroalkanesulfonyl)methide acid salt is precipitated. To isolate this, it suffices to conduct a normal operation of organic chemistry. By conducting a filtration operation (Filtration operation referred herein means a filtration operation in the recrystallization step. Hereinafter, the same.), it is possible to obtain a tris(perfluoroalkanesulfonyl)methide acid salt of a still higher purity even as compared with the above-mentioned filtration step.

Furthermore, the present inventors have obtained findings that, since the methide acid salt is partly dissolved in the solution obtained by the filtration operation, it is possible to recover the obtained filtrate and reuse it as a solvent in the recrystallization step (see the after-mentioned Table 1). By reusing, it is possible to further improve yield of tris(perfluoroalkanesulfonyl)methide acid salt and to greatly reduce waste liquid, such as waste organic solvent or waste water, even as compared with the after-mentioned Reference Example. Therefore, productivity has improved remarkably.

By subjecting a solid obtained by the recrystallization operation to vacuum drying, organic solvent or water is removed. With this, tris(perfluoroalkanesulfonyl)methide acid salt represented by formula [1] is obtained with high purity.

In the following, the present invention is explained by Examples, but the present invention is not limited by these Examples. Herein, "%" of the composition analysis values represents "mol %" of compositions obtained by measuring the reaction mixtures by nuclear magnetic resonance analyzer (NMR; in the case of no particular mention, the measurement nuclei is $^{19}F$).

EXAMPLE 1

A 300 ml, glass, reaction container with a condenser was charged with 203 g of 2M-methylmagnesium chloride-tetrahydrofuran solution under nitrogen gas stream, followed by cooling with ice. Then, 33 g of trifluoromethanesulfonyl fluoride was introduced at an inside temperature of 0-20° C. The temperature was increased once to 35-50° C., and then trifluoromethanesulfonyl fluoride was added again by 17 g. After termination of the addition, it was aged for all night at room temperature to conduct the reaction (selectivity 71%).

A 500 ml round-bottom flask was charged with 300 ml of pure water. 17.3 g of cesium chloride was added, and it was completely dissolved. Herein, the obtained reaction liquid was added, and the tetrahydrofuran in the reaction system was distilled out under reduced pressure with an evaporator (herein, 170 g of waste organic solvent was produced as a by-product). With this, cesium tris(trifluoromethanesulfonyl)methide was precipitated. The precipitated crystals were separated by filtration (herein, 320 g of waste water containing inorganic salts was produced as a by-product), followed by recrystallization with 350 g of water. The precipitated crystals were separated by filtration. Recrystallization was conducted again with 260 g of water, and the precipitated crystals were separated by filtration. The obtained crystals were dried. With this, cesium tris(trifluoromethanesulfonyl)methide was obtained with a yield of 29.7 g, a yield of 53% and a purity of 99%.

EXAMPLE 2

The reactions were conducted in the same conditions as those of Example 1, except in that rubidium chloride was used in place of cesium chloride (selectivity 76%). As a result, rubidium tris(trifluoromethanesulfonyl)methide was obtained with a yield of 58% and a purity of 99%.

EXAMPLE 3

The reactions were conducted in the same conditions as those of Example 1, except in that potassium chloride was used in place of cesium chloride (selectivity 81%). As a result, potassium tris(trifluoromethanesulfonyl)methide was obtained with a yield of 52% and a purity of 99%.

EXAMPLE 4

The reactions were conducted in the same conditions as those of Example 1, except in that pentafluoroethanesulfonyl fluoride and potassium chloride were respectively used in place of trifluoromethanesulfonyl fluoride and cesium chloride (selectivity 64%). As a result, potassium tris(pentafluoroethanesulfonyl)methide was obtained with a yield of 46% and a purity of 99%.

EXAMPLE 5

A 1000 ml, glass, reaction container with a condenser was charged with 494 g of 1.6M-methylmagnesium chloride-tetrahydrofuran solution under nitrogen gas stream, followed by cooling with ice. Then, 64 g of trifluoromethanesulfonyl fluoride was introduced at an inside temperature of 0-20° C. The temperature was increased once to 35-50° C., and then trifluoromethanesulfonyl fluoride was added again by 32 g. After termination of the addition, it was aged for all night at room temperature to conduct the reaction (selectivity 75%).

A 1000 ml round-bottom flask was charged with 500 ml of pure water. 53.2 g of tetrapropylammonium chloride was added, and it was completely dissolved. Herein, the obtained reaction liquid was added, and the tetrahydrofuran was distilled out under reduced pressure with an evaporator. To the remaining solution, 800 ml of ethyl acetate was added to conduct extraction. The obtained organic layer was evaporated, and the precipitated crystals were subjected to recrystallization with 200 ml of ethanol. The precipitated crystals were separated by filtration. The obtained crystals were dried. With this, tetrapropylammonium tris(trifluoromethanesulfonyl)methide was obtained with a yield of 73.6 g, a yield of 62%, and a purity of 97%.

EXAMPLE 6

A 300 ml, glass, reaction container with a condenser was charged with 124 g of 1.6M-methylmagnesium chloride-tetrahydrofuran solution under nitrogen gas stream, followed by cooling with ice. Then, 16 g of trifluoromethanesulfonyl fluoride was introduced at an inside temperature of 0-20° C. The temperature was increased once to 35-50° C., and then trifluoromethanesulfonyl fluoride was added again by 8 g. After termination of the addition, it was aged for all night at room temperature to conduct the reaction (selectivity 75.4%).

A 500 ml round-bottom flask was charged with 250 ml of pure water. 9.2 g of tetramethylammonium bromide was added, and it was completely dissolved. Herein, the obtained reaction liquid was added, and the tetrahydrofuran was distilled out under reduced pressure with an evaporator. To the remaining solution, 200 ml of ethyl acetate was added to conduct extraction. The obtained organic layer was evaporated, and the precipitated crystals were subjected to recrystallization with 300 ml of water. The precipitated crystals were separated by filtration. The obtained crystals were dried. With this, tetramethylammonium tris(trifluoromethanesulfonyl)methide was obtained with a yield of 26.8 g, a yield of 48%, and a purity of 99%.

As are clear in Examples 1-6, as compared with the aftermentioned Reference Example 1, it is possible to easily obtain the target product with high yield by industrially easy methods, such as filtration and recrystallization, with short steps.

REFERENCE EXAMPLE 1

A 300 ml, glass, reaction container with a condenser was charged with 200 g of 2M-methylmagnesium chloride-tetrahydrofuran solution under nitrogen gas stream, followed by cooling with ice. Then, 32 g of trifluoromethanesulfonyl fluoride was introduced at an inside temperature of 0-20° C. The temperature was increased once to 35-50° C., and then trifluoromethanesulfonyl fluoride was added again by 16 g. After termination of the addition, it was aged for all night at room temperature to conduct the reaction.

After charging a 500 ml separatory funnel with 200 g of 10% hydrochloric acid, 225 g of the reaction liquid and 72 g of isopropyl ether were added, and a liquid separation operation was conducted (herein, waste hydrochloric acid was produced by 232 g as a by-product). The obtained organic layer was washed with 450 g of water two times and with 150 g of water, and a liquid separation was conducted (herein, waste water containing organic solvent was produced by 1365 g as a by-product). Then, the organic layer was added to a 500 ml round-bottom flask and was evaporated (waste organic solvent was produced by 123 g as a by-product). To the obtained crude methide acid, 200 g of water was added. Toluene was added by 44 g×2, and a liquid separation operation was conducted two times with a separatory funnel (waste organic solvent was produced by 94 g as a by-product). To the obtained aqueous layer, 50% cesium hydroxide aqueous solution was added by 20 g for neutralization and precipitation. Then, a recrystallization was conducted by adding 60 g of water, and the precipitated crystals were separated by filtration. Again, a recrystallization was conducted by 290 g of water, and the precipitated crystals were separated by filtration. The obtained crystals were dried. With this, cesium tris(trifluoromethanesulfonyl)methide was obtained with a yield of 27.6 g and a yield of 52%.

Thus, in Reference Example 1, as compared with Examples 1-6, organic matter and waste water are drained in large amounts in the post-treatment step. Therefore, a burden is placed on industrial operation.

Herein, a comparison between Example 1 and Reference Example 1 in the amount of waste liquid is summarized in the following as Table 1.

TABLE 1

Comparison in Amount of Waste Liquid (waste liquid or filtrate after recrystallization g/1 g of methide acid salt)

|  | Example 1 | Reference Example 1 |
| --- | --- | --- |
| Waste organic solvent | 0 | 7.9 (IPE + toluene) |
| Waste water containing THF | 5.7 | 57.9 |
| Waste water containing inorganic salt | 10.8 | 0 |
| Waste liquid in total (g/g) | 16.5 | 65.8 |
| Filtrate after recrystallization (reuse)* | 20.8 | 19.6 |

IPE = diisopropyl ether
THF = tetrahydrofuran
*It shows the amount of the filtrate (usable as a recrystallization solvent of the next reaction) recovered after filtration in the recrystallization step.

As shown in Table 1, it is understood that Example 1 can greatly reduce waste liquid as compared with Reference Example 1.

The invention claimed is:
1. A method for producing a tris(perfluoroalkanesulfonyl)methide acid salt represented by formula [1]

$$[RfSO_2]_3C_nM \quad [1]$$

wherein Rf represents a $C_{1-9}$ straight-chain or branched-chain perfluoroalkyl group, n represents an integer that is identical with valence of the corresponding cation, and
M is a cation representing an alkali metal, quaternary ammonium represented by $(R^1)_4N$, or quaternary phosphonium represented by $(R^1)_4P$, $R^1$'s represent $C_{1-9}$, identical or different, straight-chain or branched-chain, saturated or unsaturated aliphatic hydrocarbon groups or aryl groups and hydrogen atoms of $R^1$'s may partially or entirely be replaced with halogen, alkyl group, amino group, nitro group, acetyl group, cyano group or hydroxyl group, comprising the steps of:
(a) reacting a methylmagnesium halide represented by formula [2]

$$CH_3MgX \quad [2]$$

wherein X represents a chlorine, bromine or iodine,
with a perfluoroalkanesulfonyl fluoride represented by formula [3]

$$RfSO_2F \quad [3]$$

wherein Rf represents a $C_{1-9}$ straight-chain or branched-chain perfluoroalkyl group, thereby obtaining a reaction mixture containing a tris(perfluoroalkanesulfonyl)methide acid magnesium halide represented by formula [4]

$$[RfSO_2]_3C(MgX) \quad [4]$$

wherein Rf and X are defined as above; and
(b) directly reacting the tris(perfluoroalkanesulfonyl)methide acid magnesium halide from step (a) with at least one salt selected from the group consisting of alkali metal halides, quaternary ammonium salts, and quaternary phosphonium salts, by directly adding the at least one salt to the obtained reaction mixture from step (a),
wherein the quaternary ammonium salts of step (b) are represented by the formula of $(R^1)_4N^+.X'^-$ where $R^1$'s are defined as above, and X' represents a halogen, acetate, alkanesulfonate, or arylsulfonate, and hydrogen atoms of X' may partially or entirely be replaced with halogen, alkyl group, amino group, nitro group, acetyl group, cyano group or hydroxyl group,
wherein the quaternary phosphonium salts of step (b) are represented by the formula of $(R^1)_4P^+.X'^-$ where $R^1$'s and X' are defined as above.

2. A method according to claim 1, wherein the alkali metal as M in formula [1] is at least one selected from the group consisting of lithium, sodium, potassium, rubidium, and cesium.

3. A method according to claim 1, wherein the alkali metal halide of the step (b) is at least one selected from the group consisting of lithium fluoride, lithium chloride, lithium bromide, lithium iodide, sodium fluoride, sodium chloride, sodium bromide, sodium iodide, potassium fluoride, potassium chloride, potassium bromide, potassium iodide, rubidium fluoride, rubidium chloride, rubidium bromide, rubidium iodide, cesium fluoride, cesium chloride, cesium bromide, and cesium iodide.

4. A method according to claim 1, wherein the quaternary ammonium salt of the step (b) is at least one selected from the group consisting of tetramethylammonium fluoride, tetramethylammonium chloride, tetramethylammonium bromide, tetramethylammonium iodide, tetraethylammonium fluoride, tetraethylammonium chloride, tetraethylammonium bromide, tetraethylammonium iodide, tetrapropylammonium fluoride, tetrapropylammonium chloride, tetrapropylammonium bromide, tetrapropylammonium iodide, tetrabutylammonium fluoride, tetrabutylammonium chloride, tetrabutylammonium bromide, and tetrabutylammonium iodide.

5. A method according to claim 1, wherein the quaternary phosphonium salt of the step (b) is at least one selected from the group consisting of tetraphenylphosphonium fluoride, tetraphenylphosphonium chloride, tetraphenylphosphonium bromide, tetraphenylphosphonium iodide, tetrabutylphosphonium fluoride, tetrabutylphosphonium chloride, tetrabutylphosphonium bromide, tetrabutylphosphonium iodide, butyltriphenylphosphonium fluoride, butyltriphenylphosphonium chloride, butyltriphenylphosphonium bromide, butyltriphenylphosphonium iodide, trioctylethylphosphonium fluoride, trioctylethylphosphonium chloride, trioctylethylphosphonium bromide, trioctylethylphosphonium iodide, benzyltriphenylphosphonium fluoride, benzyltriphenylphosphonium chloride, benzyltriphenylphosphonium bromide, benzyltriphenylphosphonium iodide, ethyltriphenylphosphonium fluoride, ethyltriphenylphosphonium chloride, ethyltriphenylphosphonium bromide, and ethyltriphenylphosphonium iodide.

6. A method according to claim 1, wherein the methylmagnesium halide of the step (a) is methylmagnesium chloride.

7. A method according to claim 1, wherein the perfluoroalkanesulfonyl fluoride of the step (a) is trifluoromethanesulfonyl fluoride.

8. A method according to claim 1, wherein a product of the step (b) is subjected to filtration and a recrystallization from water.

9. A method for producing a tris(perfluoroalkanesulfonyl)methide acid salt represented by formula [1]

$$[RfSO_2]_3C_nM \qquad [1]$$

wherein Rf represents a $C_{1-9}$ straight-chain or branched-chain perfluoroalkyl group, n represents an integer that is identical with valence of the corresponding cation, and M is a cation representing an alkali metal, quaternary ammonium represented by $(R^1)_4N$, or quaternary phosphonium represented by $(R^1)_4P$, $R^1$'s represent $C_{1-9}$, identical or different, straight-chain or branched-chain, saturated or unsaturated aliphatic hydrocarbon groups or aryl groups, and hydrogen atoms of $R^1$'s may partially or entirely be replaced with halogen, alkyl group, amino group, nitro group, acetyl group, cyano group or hydroxyl group, consisting of the steps of:

(a) reacting a methylmagnesium halide represented by formula [2]

$$CH_3MgX \qquad [2]$$

wherein X represents a chlorine, bromine or iodine,
with a perfluoroalkanesulfonyl fluoride represented by formula [3]

$$RfSO_2F \qquad [3]$$

wherein Rf represents a $C_{1-9}$ straight-chain or branched-chain perfluoroalkyl group, thereby obtaining a reaction mixture; and (b) directly reacting the obtained reaction mixture from step (a) with at least one salt selected from the group consisting of alkali metal halides, quaternary ammonium salts, and quaternary phosphonium salts,
wherein the quaternary ammonium salts of step (b) are represented by the formula of $(R^1)_4N^+.X'^-$ where $R^1$'s are defined as above, and X' represents a halogen, acetate, alkanesulfonate, or arylsulfonate, and hydrogen atoms of X' may partially or entirely be replaced with halogen, alkyl group, amino group, nitro group, acetyl group, cyano group or hydroxyl group,
wherein the quaternary phosphonium salts of step (b) are represented by the formula of $(R^1)_4P^+.X'^-$ where $R^1$'s and X' are defined as above.

10. The method according to claim 9, wherein the obtained reaction mixture from step (a) comprises a tris(perfluoroalkanesulfonyl)methide acid magnesium halide represented by formula [4]

$$[RfSO_2]_3C(MgX) \qquad [4]$$

wherein Rf is the same as above, and X represents a chlorine, bromine or iodine.

11. The method according to claim 9, wherein the alkali metal as M in formula [1] is at least one selected from the group consisting of lithium, sodium, potassium, rubidium, and cesium.

12. The method according to claim 9, wherein the alkali metal halide of the step (b) is at least one selected from the group consisting of lithium fluoride, lithium chloride, lithium bromide, lithium iodide, sodium fluoride, sodium chloride, sodium bromide, sodium iodide, potassium fluoride, potassium chloride, potassium bromide, potassium iodide, rubidium fluoride, rubidium chloride, rubidium bromide, rubidium iodide, cesium fluoride, cesium chloride, cesium bromide, and cesium iodide.

13. The method according to claim 9, wherein the quaternary ammonium salt of the step (b) is at least one selected from the group consisting of tetramethylammonium fluoride, tetramethylammonium chloride, tetramethylammonium bromide, tetramethylammonium iodide, tetraethylammonium fluoride, tetraethylammonium chloride, tetraethylammonium bromide, tetraethylammonium iodide, tetrapropylammonium fluoride, tetrapropylammonium chloride, tetrapropylammonium bromide, tetrapropylammonium iodide, tetrabutylammonium fluoride, tetrabutylammonium chloride, tetrabutylammonium bromide, and tetrabutylammonium iodide.

14. The method according to claim 9, wherein the quaternary phosphonium salt of the step (b) is at least one selected from the group consisting of tetraphenylphosphonium fluoride, tetraphenylphosphonium chloride, tetraphenylphosphonium bromide, tetraphenylphosphonium iodide, tetrabutylphosphonium fluoride, tetrabutylphosphonium chloride, tetrabutylphosphonium bromide, tetrabutylphosphonium iodide, butyltriphenylphosphonium fluoride, butyltriphenylphosphonium chloride, butyltriphenylphosphonium bromide, butyltriphenylphosphonium iodide, trioctylethylphosphonium fluoride, trioctylethylphosphonium chloride, trioctylethylphosphonium bromide, trioctylethylphosphonium iodide, benzyltriphenylphosphonium fluoride, benzyltriphenylphosphonium chloride, benzyltriphenylphosphonium bromide, benzyltriphenylphosphonium iodide, ethyltriphenylphosphonium fluoride, ethyltriphenylphosphonium chloride, ethyltriphenylphosphonium bromide, and ethyltriphenylphosphonium iodide.

15. The method according to claim 9, wherein the methylmagnesium halide of the step (a) is methylmagnesium chloride.

16. The method according to claim 9, wherein the perfluoroalkanesulfonyl fluoride of the step (a) is trifluoromethanesulfonyl fluoride.

17. The method according to claim 9, wherein a product of the step (b) is subjected to filtration and a recrystallization from water.

* * * * *